(12) United States Patent
Vickery

(10) Patent No.: US 6,203,820 B1
(45) Date of Patent: Mar. 20, 2001

(54) COMPOSITIONS AND METHODS FOR ENHANCING PROTEIN ANABOLISM AND DETOXIFICATION

(76) Inventor: Brice E. Vickery, 007 W. Ridge Ct., Parachute, CO (US) 81635

( * ) Notice: Subject to any disclaimer, the term of this patent is extended or adjusted under 35 U.S.C. 154(b) by 0 days.

(21) Appl. No.: 09/317,595

(22) Filed: May 24, 1999

Related U.S. Application Data

(63) Continuation of application No. 09/085,845, filed on May 28, 1998, now abandoned.
(51) Int. Cl.$^7$ .................. A61K 33/26; A61K 31/415; A61K 31/195
(52) U.S. Cl. ............... 424/646; 514/400; 514/561; 514/562; 514/565
(58) Field of Search ................ 424/646; 514/400, 514/561, 562, 565

(56) References Cited

U.S. PATENT DOCUMENTS

| | | | |
|---|---|---|---|
| 4,514,421 | 4/1985 | Herschler | 514/711 |
| 4,767,704 | 8/1988 | Cleveland et al. | 435/68 |
| 5,071,878 | 12/1991 | Herschler | 514/711 |
| 5,576,351 | 11/1996 | Yoshimura et al. | 514/565 |
| 5,922,766 * | 7/1999 | Acosta et al. | 514/561 |

OTHER PUBLICATIONS

Berger, S., Dr. Berger's Immune Power Diet, New American Library, 1985, pp. 224–230.
Braverman, E. et al., "The Healing Nutrients Within, Facts, Findings and New Research on Amino Acids", Keats Publishing, Inc., 1987, pp. 6, 97–113, and 118–119.
Bremer, H. et al., "Disturbances of Amino Acid Metabolism: Clinical Chemistry and Diagnosis", Urban & Schwarzenberg, 1981, pp. 203–204.
Chaitow, L., "Amino Acids in Therapy, A Guide to the Therapeutic Application of Protein Constitutents", Thorsons Publishers, Inc., 1985, pp. 12–13, 19, 24, 27–32, and 42.
Erdmann, R. et al., "The Amino Revolution, The Breakthrough Program that will Change the Way You Fell", Contemporary Books, Inc., 1987, pp. 14–17.
Guyton, A., Textbook of Medical Physiology, Seventh Edition, W.B. Saunders Company, 1986, p. 795.
Klein, A. et al., "Backache Relief, the Ultimate Second Opinion from Back–Pain Sufferers Nationwide Who Share their Successful Healing Experiences", Times Books, 1985, pp. 20, 22, 26–28, 34–36, and 103.
Kramer, J., "Intervertebral Disk Diseases, Causes, Diagnosis, Treatment and Prophylaxis", Year Book Medical Publishers, Inc., 1981, pp. 15–16, 38, 49, and 55.
Lau, B., "Garlic for Health", Benjamin Lau, M.D., Ph.D., 1998, pp. 32–35.
Leonhardt, H. et al., "Fundamentals of Electroacupuncture According to Voll", Medizinisch Literarische Verlagsgesellschaft mbH, Uelzen, 1980, pp. 187–188.

Loomis, H., "Sulfur or Sulfate? Enzyme Therapy", The American Chiropractor, Sep./Oct., 1997, pp. 32 and 34.
Mindell, E., "The MSM Miracle, Enhance your Health with Organic Sulfur", Keats Publishing, Inc., 1997, pp. 8–21.
Murray, M., Encyclopedia of Nutritional Supplements, Prima Publishing, 1996, pp. 218–221.
Pressman, A. et al., "The GSH Phenomenon, Nature's Most Powerful Antioxidant and Healing Agent", St. Martin's Press, 1997, pp. ix, 2–15, 23–30, 47–48, and 85–86.
Reuveny, Z., "Derepression of ATP sulfurylase by the sulfate analogs molybdate and selenate in cultured tobacco cells", Proc. Natl. Acad. Science, USA, Cell Biology, vol. 74, No. 2, Feb., 1977, pp. 619–622.
Sahelian, R. et al., "Creatine, Nature's Muscle Builder", Ray Sahelian, M.D. and Dave Tuttle, 1997, pp. 75–76, 78–80, and 82–85.
Schmid, R., "Lectures of Dr. Jeffrey Bland, Compiled and Interpreted by Ronald F. Schmid, N.D.", Ronald F. Schmid, $1^{st}$ ed., Jun., 1980, pp. 81–82.
Schramm, H–J., "Kinesiology for Patients of a General Practice: Empirical Findings", Biomedical Therapy, vol. XVI, No. 1, 1998, pp. 139–145.
Vickery, B., "Amino Acids, the New Foundation for Healing and Wellness", The American Chiropractor, Nov./Dec., 1998, pp. 20–22 and 44.
Vickery, B., "The BEV Tests", The Collected Papers of the International College of Applied Kinesiology, vol. I, Summer, 1990–1991, pp. 224–234.
Vickery, B., "The Comfirmatory Challenge Test", Collected Papers of the Members of the International College of Applied Kinesiology–USA, vol. I, Summer, 1989–90, pp. 259–266.
Vickery, B., "Disc Lesions: A Key to Low Back Problems", Today's Chiropractic, vol., 16, No. 2, May/Jun., 1987, 4 pages.
Vicery, B., "Free Form Amino Acids—The Key Dietary Supplement", Balance, Mar./Apr., 1989, pp. 10–11.
Vickery, B., "The Diskal Lesion—A Perfect Foundaiton for $21^{st}$ Century Chiropractic and Osteopathy", The American Chiropractor, Sep., 1991, pp. 5–10.

(List continued on next page.)

Primary Examiner—Raymond Henley, III
(74) Attorney, Agent, or Firm—Christie, Parker & Hale, LLP

(57) ABSTRACT

A composition for enhancing protein anabolism and detoxification comprises molybdenum and at least two amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine. Preferably the composition further comprises creatine and/or sulfur. Preferably the amino acids are all free form amino acids. The composition is provided in the form of a powder, which is preferably encapsulated in a gelatin capsule. Methods for enhancing protein anabolism and/or detoxification in a patient comprise administering to the patient an effective amount of a composition as described above. The composition is preferably administered orally in an amount of from about 3 grams/day to about 10.5 grams/day.

43 Claims, 1 Drawing Sheet

OTHER PUBLICATIONS

Vicery, B., "The Grading of Intervertebral Disc Lesions", Collected Papers of the International College of Applied Kinesiology, Summer, 1986, pp. 281–283.

Vickery, V., "A Study of the Intervertebral Disk Lesion", Today's Chiropractic, vol. 18, No. 5, Sep./Oct., 1989, 6 pages.

Vicery, B., "The Vickery Method of Chiropractic and Osteopathy: Challenging The Professions to Enter the 21$^{st}$ Century Now!", *The American Chiropractor*, vol. 14, No. 5, May, 1992, pp. 10–12 and 14.

Vickery, B., "The Vickery Method of Chiropractic and Osteopathy", The Digest of Chiropractic Economics, Sep./Oct., 1991, pp. 32–37.

Vickery, B., Label from Essential Amino Acids Formula (no date).

Walther, D., "Applied Kinesiolgoy", Synopsis, Systems DC, 1988, pp. ix–xii.

G.M. Bressa, "S–adenosyl–l–methionine (SAMe) as antidepressant: meta–analysis of clinical studies", Acta Neurol Scand Suppl, 1994;154:7–14. (Abstract).

K.M. Bell et al., "S–adenosylmethionine blood levels in major depression: changes with drug treatment", Acta Neurol Scand Suppl, 1994; 154:15–8. (Abstract).

T. Bottiglieri et al., "The clinical potential of ademethionine (S–adenosylmethionine) in neurological disorders", Drugs, Aug 1994; 48(2):137–52. (Abstract).

B.L. Kagan et al, "Oral S–adenosylmethionine in depression: a randomized, double–blind, placebo–controlled trial", Am J Psychiatry May 1990;147(5):591–5. (Abstract).

J.F. Rosenbaum et al., "The antidepressant potential of oral S–adenosyl–l–methionine", Acta Psychiatr Scand May 1990;81(5):432–6. (Abstract).

M. Fava et al., "Neuroendocrine effects of S–adenosyl–L–methionine, a novel putative antidepressant", J Psychiatr Res 1990;24(2):177–84. (Abstract).

G.L. Cantoni et al., "Affective disorders and S–adenosylmethionine: a new hypothesis", Trends Neurosci Sep 1989;12(9):319–24. (Abstract).

D. De Leo, "Treatment of adjustment disorders: A comparative evaluation", Psychol Rep Feb 1989 ;64(1):51–4. (Abstract).

K.M. Bell et al., "S–adenosylmethionine treatment of depression: a controlled clinical trial", Am J Psychiatry Sep 1988;145(9):1110–4. (Abstract).

M. Fava et al., "Rapidity of onset of the antidepressant effect of parenteral S–adenosyl–L–methionine", Psychiatry Res Apr. 28, 1995; 56(3)295–7. (Abstract).

C. Berlanga et al., "Efficacy of S–adenosyl–L–methionine in speeding the onset of action of imipramine", Psychiatry Res Dec 1992;44(3):257–62. (Abstract).

C.A. Cooney et al., "Methamphetamine treatment affects blood and liver S–adenosylmethionine (SAM) in mice. Correlation with dopamine depletion in the striatum", Ann N Y Acad Sci May 30, 1998;844:191–200. (Abstract).

T. Bottiglieri et al., "Cerebrospinal fluid S–adenosylmethionine in depression and dementia: effects of treatment with parenteral and oral S–adenosylmethionine", J Neurol Neurosurg Psychiatry Dec. 1990;53(12):1096–8. (Abstract).

B.M. Cohen et al., "Effects of the novel antidepressant S–adenosyl–methionine on alpha 1– nad beta–adrenoceptors in rat brain", Eur J Pharmacol Nov. 7, 1989;170(3):201–7. (Abstract).

M.W. Carney et al., "S–adenosylmethionine and affective disorder", Am J Med Nov. 20, 1987; 83(5A):104–6. (Abstract).

F. Dainous et al., "Effect of modification of membrane phospholipid composition on phospholipid methylation in aggregating cell culture", J Neurochem Jun. 1986;46(6):1859–64. (Abstract).

M. Valchar, "What is next in the development of antidepressives?", [Article in Czech], Biochem Pharmacol May 15, 1983;32(10):1581–5. (Abstract).

A. Czyrak et al., "Antidepressant activity of S–adenosyl–L–methionine in mice and rats", J Basic Clin Physiol Pharmacol Jan.–Mar. 1992;3(1):1–17. (Abstract).

C. Arpino et al., "Use and misuse of antidepressant drugs in a random sample of the population of Rome, Italy", Acta Psychiatr Scand Jul. 1995;92(1):7–9. (Abstract).

R.A. Bodner et al., "Serotonin syndrome", Neurology Feb. 1995;45(2):219–23. (Abstract).

M.S. Yassin et al., "Inhibitors of catecholamine metabolizing enzymes cause chages in S–adenosylmethionine and S–adenosylhomocysteine in the rat brain", Neurochem Int Jan. 1998;32(1):53–9. (Abstract).

T. Doi et al., "Effect of vitamin B12 deficiency on S–adenosylmethionine metabolism in rats", J Nutr Sci Vitaminol (Tokyo) Feb. 1989;35(1)1–9. (Abstract).

M.W. Carney et al., "The switch mechanism and the bipolar/unipolar dichotomy", Br J Psychiatry Jan. 1989;154:48–51. (Abstract).

T. Bottiglieri, "Folate, vitamin B12, and neuropsychiatric disorders", Nutr Rev Dec. 1996 ;54(120):382–90. (Abstract).

P.J. Goodnick et al., "Psychotropic treatment of chronic fatigue syndrome and related disorders", Clin Psychiatry Jan. 1993;54(1):13–20. (Abstract).

O.A. Hietala et al., "The inverse changes of mouse brain ornithine and S–adenosylmethionine decarboxylase activities by chlorpromazine and imipramine. Dependence of ornithine decarboxylase induction on beta–adrenoceptors", Biochem Pharmacol May 15, 1983; 32(10):1581–5. (Abstract).

Nature–made SAM–e advertisement (photocopy, 1 page, no date).

Energy Times, Nutrition 101, "Meet SAMe, New Mood Booster", Energy Times, Oct. 1999 (photocopy, 1 page).

* cited by examiner

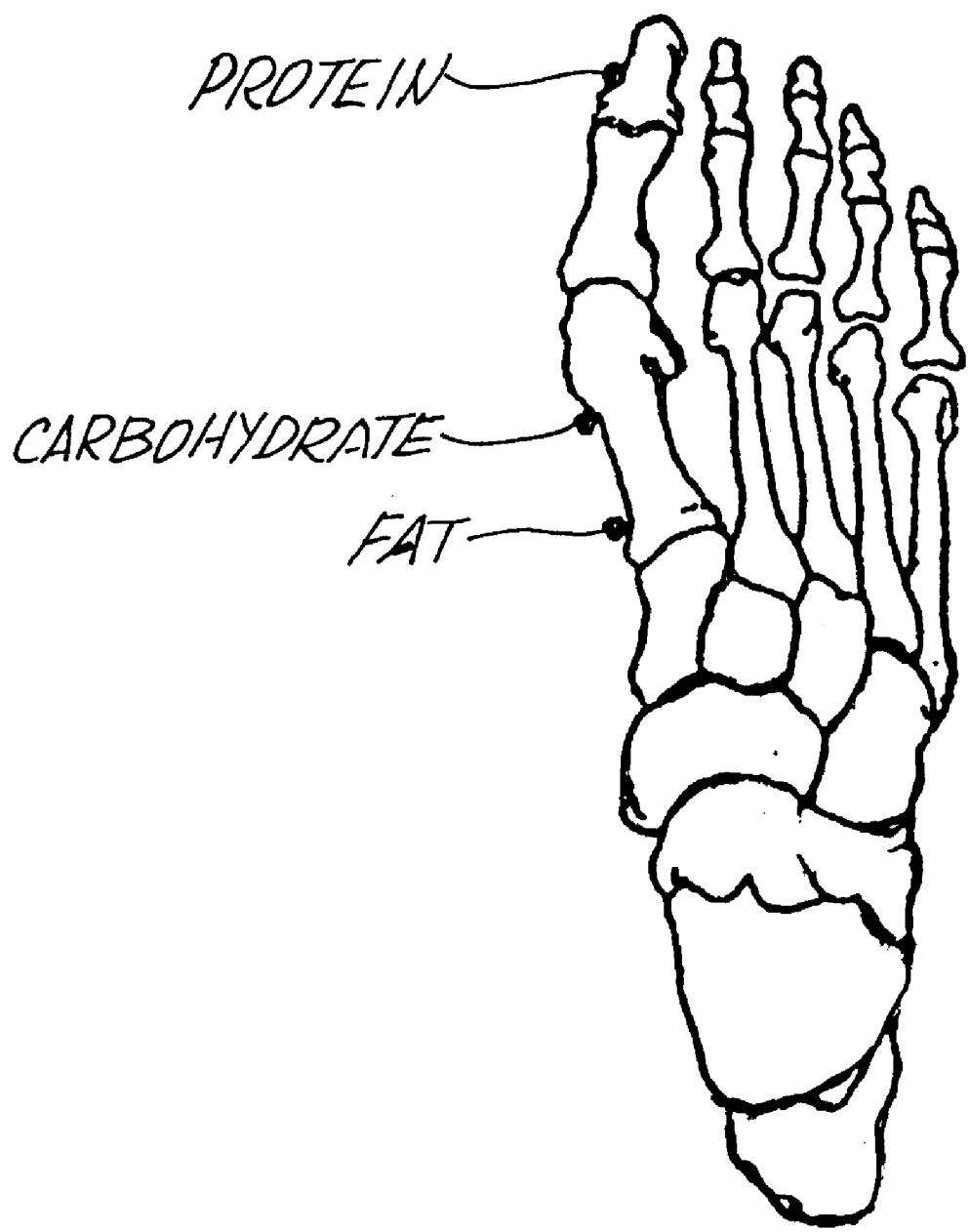

COMPOSITIONS AND METHODS FOR ENHANCING PROTEIN ANABOLISM AND DETOXIFICATION

This is a continuation of U.S. Application Ser. No. 09/085,845 filed May 28, 1998, now abandoned.

FIELD OF THE INVENTION

The present invention is directed to amino acid compositions useful for enhancing protein anabolism and detoxification.

BACKGROUND OF THE INVENTION

For the last century, the role of vitamins, minerals and essential fatty acids as dietary necessities has been progressively recognized, and supplementation of these nutrients is becoming accepted procedure. Conventional wisdom dictates that dietary intake of between about 30 and 55 grams of protein per day ensures adequate protein for all of the body's functions. In the treatment of protein-deficient patients, it has been found that free form amino acids are superior to maintain sufficient protein levels as compared to protein supplied in complex large molecules. Dietary proteins are not used directly but must be broken down into their constituent individual amino acids in order to be absorbed and utilized by the body. Free form amino acids, in contrast, are individual, single amino acids with no fillers or allergens, and are immediately absorbable by the gut. Upon absorption, the amino acids are carried rapidly in the blood plasma to the cells where they are used or stored. Free amino acids are the building blocks of more complex protein molecules that perform structural or functional roles in tissue. Free form amino acids are presently commercially available.

The amino acid proportions of the blood plasma differ significantly from the profiles of either food proteins or the various body proteins. Pools of amino acids in body tissues are needed for normal anabolic function. This pool is normally replaced by the blood's supply of amino acids. The blood, in turn, draws from pools of free amino acids in other tissues to replace what has been used. Therefore plasma concentrations of amino acids remain relatively constant even the supply through dietary sources is deficient for any reason. Thus, the standard accepted total protein tests of the plasma do not provide an early warning of protein and amino acid deficiencies.

Excess of some amino acids can produce results as detrimental as some deficiencies. Balance in the use of amino acids is of the greatest importance. Thus, a need exists for a superior nutritional formulation that can be used to provide amino acids for enhancing protein anabolism.

Another concern is detoxification, namely, the removal of toxic substances such as alcohol and pesticides from the body. Detoxification occurs in the liver in two phases. During Phase I, the liver cells secrete cytochrome P-450 enzymes, which convert waste products to more soluble forms so that they can be excreted by the colon and kidneys. During Phase II, glutathione and other enzymes in the liver corral free radicals, heavy metals, and some toxic wastes and remove them from the body. Critical to this process is the conversion of sulfites to sulfates. Molybdenum is a component of enzymes that assist in this conversion. Thus, a need also exists for a nutritional formulation that provides a sufficient supply of molybdenum to create the necessary enzymes to assist with Phase II detoxification.

SUMMARY OF THE INVENTION

The present invention is directed to a composition for enhancing protein anabolism. The composition comprises molybdenum and at least two amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine. Preferably the composition further comprises creatine monohydrate and/or sulfur, preferably in the form of methylsulfonylmethane.

It is desirable to include all of the above-listed amino acids in the composition. In a particularly preferred embodiment, the composition comprises, based on the total weight of the composition:

about 6% to about 9% by weight L-arginine,
about 2% to about 4% by weight L-cystine,
about 1.5% to about 3.5% by weight L-histidine,
about 6% to about 9% by weight L-isoleucine,
about 8% to about 12% by weight L-leucine,
about 6% to about 8% by weight L-lysine,
about 2.5% to about 4.5% by weight L-methionine,
about 5.5% to about 7.5% by weight L-phenylalanine,
about 4.5% to about 6.5% by weight L-threonine,
about 4% to about 6% by weight L-tyrosine,
about 7% to about 10% by weight L-valine,
about 0.001% to about 0.03% by weight molybdenum,
about 3% to about 30% by weight creatine monohydrate, and
about 5% to about 45% by weight methylsulfonylmethane. Preferably the amino acids are all free form amino acids. Alternatively, the amino acids can be provided in the form of powdered egg white or powdered milk, for example, in the event that free form amino acids are not available. When the amino acids are provided in this converted form, the composition preferably further comprises a proteolytic enzyme.

The composition of the invention is provided in the form of a powder, which is preferably encapsulated in a gelatin capsule.

The invention is also directed to a method for enhancing protein anabolism in a patient comprising administering to the patient an effective amount of a composition as described above. The composition is preferably administered orally. Preferably the composition is administered to the patient in an amount of from about 1.5 grams/day to about 15 grams/day, more preferably in an amount of from about 3 grams/day to about 10.5 grams/day.

BRIEF DESCRIPTION OF THE DRAWING

These and other features and advantages of the present invention will be better understood by reference to the following detailed description when considered in conjunction with the accompanying drawing, wherein:

FIG. 1 is an illustration of the Voll Points on the foot, used in the Vickery-Voll Test.

DETAILED DESCRIPTION OF THE INVENTION

The present invention is directed to a composition for enhancing protein anabolism. The composition comprises molybdenum and at least two amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine. Molybdenum activates enzymes in the liver that assist in and enhance the detoxification process. The molybdenum can be provided in any suitable form, for example, as sodium molybdate or etrathiolmolybdate. A particularly useful form is Kreb's (available from Douglas Laboratories under the trade name VitaHealthy or from Monarch Nutrition, Utah), which is a complex formed from sodium molybdate, alphaketoglutaric acid, citric acid, fumaric acid, malic acid, succinate and dicalcium phosphate. The molybdenum is present in the composition in an amount of from about 0.001% to about 0.03% by weight, more preferably from about 0.0015% to about 0.01% by weight, based on the total weight of the active ingredients in the composition.

L-Arginine is desirable in the composition for stimulating the immune system and assisting in the utilization of other amino acids. L-Arginine has several other advantages, including blocking the formation of tumors, causing release of growth hormone, forming citrulline and ornithine by hydrolysis, detoxification of ammonia, assisting in liver regeneration, wound healing, growth and sperm formation, and lowering cholesterol. L-Arginine is preferably present in the composition in an amount ranging from about 6% to about 9% by weight, more preferably from about 7% to about 8% by weight, based on the total weight of the active ingredients in the composition.

L-Cystine is convertible to and from cysteine. L-Cystine is believed to minimize the cross-linking of free radicals that age the skin, harden the arteries, deposit aging pigments, and cause arthritis and mutagenic disorders such as cancer. Additionally, L-cystine is the precursor of glutathione, the body's primary antioxidizer and detoxifier that protects against such substances as lead, mercury, radiation, pesticides, and tobacco smoke. L-Cystine is also important in red and white cell formation and facilitating oxygen transport. L-Cystine is preferably present in the composition in an amount ranging from about 2% to 4%, more preferably from about 2.5% to about 3.5%, based on the total weight of the active ingredients in the composition.

L-Histidine is a necessary amino acid for neurotransmitter formation. Additionally, L-histidine regulates blood sugar levels and affects allergic response. L-Histidine is preferably present in the composition in an amount of from about 1.5% to about 3.5% by weight, more preferably from about 2% to about 3% by weight, based on the total weight of the active ingredients in the composition.

L-Isoleucine aids in wound healing and muscle growth. Additionally, L-isoleucine is critical to life in stress, energy and muscle metabolism. L-Isoleucine is preferably present in the composition in an amount of from about 6% to about 9% by weight, more preferably from about 7% to about 8% by weight, based on the total weight of the active ingredients in the composition.

L-Leucine is useful for lowering blood sugar, stimulating protein synthesis in muscle, and wound healing of skin and bone. Additionally, L-leucine stimulates protein synthesis in muscle. L-Leucine is preferably present in the composition in an amount of from about 8% to about 12% by weight, more preferably from about 9% to about 11% by weight, based on the total weight of the active ingredients in the composition.

L-Lysine is a critical enzyme in carbohydrate metabolism. L-Lysine is used in the treatment of herpes viruses and Parkinsons' Psychosis. Additionally, L-lysine builds connective tissue, collagen and bone and assists in calcium transport through the body. L-Lysine is preferably present in the composition in an amount of from about 6% to 8% by weight, more preferably from about 6.5% to about 7.5% by weight, based on the total weight of the active ingredients in the composition.

L-Methionine is a sulfur-containing amino acid that removes heavy metals, quenches free radicals, and lowers cholesterol. L-Methionine also prevents fat accumulation in the liver and, along with cysteine/cystine, helps prevent disorders of the hair, skin, and nails. L-Methionine is preferably present in the composition in an amount of from about 2.5% to 4.5% by weight, more preferably from about 3% to about 4% by weight, based on the total weight of the active ingredients in the composition.

L-Phenylalanine is useful for synthesizing insulin, adrenaline and certain enzymes. Additionally, L-phenylalanine enhances alertness, learning and memory and acts as a pain retardant and appetite suppressant. L-Phenylalanine also helps build collagen and connective tissues. L-Phenylalanine is preferably present in the composition in an amount of from about 5.5% to about 7.5% by weight, more preferably from about 6% to about 7% by weight, based on the total weight of the active ingredients in the composition.

L-Threonine is useful as an immune booster. It degrades into glycine, serine, and glucose. L-Threonine is a wound healer and decreases the harmful effects of aspirin. L-Threonine is preferably present in the composition in an amount of from about 4.5% to about 6.5% by weight, more preferably from about 5% to about 6% by weight, based on the total weight of the active ingredients in the composition.

L-Tryptophan is a precursor to melatonin and serotine. Additionally, L-tryptophan acts as an appetite suppressant, growth hormone stimulant and platelet clotting factor. L-Tryptophan can also be sued to treat insomnia, depression, migraine headaches, and high blood pressure. L-Tryptophan is preferably in the composition in an amount of from about 0.8% to about 3% by weight, more preferably in an amount of from about 1.5% to about 2.5% by weight, based on the total weight of the active ingredients in the composition. If desired, 5-hydroxytryptophan can be used instead of L-tryptophan.

L-Tyrosine is a precursor for dopamine, norepinephrine, thryoxin, catacholestrogens, melanin, and enkephalines. L-Tyrosine can be used as an antidepressant, a growth hormone promoter, an appetite suppressant, or an antioxidant. L-Tyrosine is preferably present in the composition in an amount of from about 4% to about 6% by weight, more preferably from about 4.5% to about 5.5% by weight, based on the total weight of the active ingredients in the composition.

L-Valine aids in would healing, muscle growth and liver diseases. L-Valine is preferably present in the composition in an amount of from about 7% to about 10% by weight, more preferably from about 8% to about 9% by weight, based on the total weight of the active ingredients in the composition.

If available as both a base and a hydrochloride, each amino acid is preferably used in the base form. The amino acids are preferably in the form of free form amino acids. Alternatively, the amino acids can be provided in converted form. The converted amino acids can be supplied, for example, in the form of egg white powder or milk powder. If the amino acids are provided in converted form, preferably the composition further comprises a proteolytic enzyme in an amount of from about 15% to about 25%, based on the total weight of the active ingredients in the composition.

Preferably the composition contains at least three, more preferably at least four, still more preferably at least five, and even more preferably at least six, of the above-listed amino acids. In a particularly preferred embodiment, the composition contains all of the above-listed amino acids. In another particularly preferred embodiment, the composition contains all of the above-listed amino acids except L-tryptophan.

Preferably the composition further comprises creatine. Creatine is a natural body substance found to be distributed primarily in the skeletal muscle. Creatine assists in the replenishment of adenosine triphosphate, an energy source used in protein synthesis, in the muscles. Creatine has no known side effects. Preferably the creatine is in the form of creatine monohydrate. Preferably the creatine is present in the composition in an amount of from about 3% to about 30% by weight, more preferably from about 12% to about 22% by weight, based on the total weight of the active ingredients in the composition.

Preferably the composition also comprises sulfur in addition to the sulfur provided in any of the amino acids. Sulfur is present in every cell of the body and is necessary for collagen synthesis. The body turns over approximately 850 mg of sulfur a day, resulting in a daily deficit. Food alone cannot always overcome this deficit. The sulfur can be provided in any suitable form, for example, as methylsulfonylmethane. Preferably sulfur is present in the composition in an amount of from about 1.5% to about 15%, more preferably from about 5% to about 10% by weight, based on the total weight of the active ingredients in the composition. If methylsulfonylmethane is used as the source of sulfur, preferably the methylsulfonylmethane is present in the composition in an amount of from about 5% to about 45% by weight, more preferably from about 15% to about 30% by weight, based on the total weight of the active ingredients in the composition.

A particularly preferred composition according to the invention comprises about 6% to about 9% by weight L-arginine, about 2% to about 4% by weight L-cystine, about 1.5% to about 3.5% by weight L-histidine, about 6% to about 9% by weight L-isoleucine, about 8% to about 12% by weight L-leucine, about 6% to about 8% by weight L-lysine, about 2.5% to about 4.5% by weight L-methionine, about 5.5% to about 7.5% by weight L-phenylalanine, about 4.5% to about 6.5% by weight L-threonine, about 4% to about 6% by weight L-tyrosine, about 7% to about 10% by weight L-valine, about 0.001% to about 0.03% by weight molybdenum, about 3% to about 30% by weight creatine, about 5% to about 45% by weight methylsulfonylmethane, and optionally about 0.8% to about 3% by weight L-tryptophan or 5-hydroxytryptophan, based on the total weight of the active ingredients in the composition.

Another composition according to the invention comprises about 40% to about 55% by weight powdered egg white or powdered milk, about 15% to about 25% by weight of a proteolytic enzyme, about 20% to about 45% by weight methylsulfonylmethane, about 5% to about 15% by weight creatine, and from about 0.0015% to about 0.0050% by weight molybdenum, based-on the total weight of the active ingredients in the composition.

As used herein, the term "active ingredients" refers to the following: L-arginine, L-cystine, L-histidine, L-isoleucine, L-leucine, L-lysine, L-methionine, L-phenylalanine, L-threonine, L-tryptophan, L-tyrosine, L-valine, molybdenum, creatine, creatine monohydrate, sulfur, and methylsulfonylmethane. When the term "active ingredients" is used in connection with a composition comprising powdered egg white or powdered milk, the term also encompasses powdered egg white, powdered milk, and proteolytic enzymes.

The compositions according to the invention can be made by any suitable method known to those skilled in the art. For example, the free form amino acids, as well as the methylsulfonylmethane, creatine monohydrate, and molybdenum, are provided in the form of a powder. Similarly, the powdered egg white, powdered milk and proteolytic enzyme are available in powder form. For relatively small batches (e.g., less than 10 kilos), the desired amount of each component is measured and put into a large plastic bag. The plastic bag is sealed with a large amount of air remaining in the bag. The bag is then shaken and tossed for about ten minutes to thoroughly mix the composition. For larger batches, the components can be mixed in a large stainless steel mixer.

The blended composition can then be provided in any suitable dosage form. For example, if an oral dosage form is desired, the composition can be contained within gelatin capsules, preferably ones that do not deteriorate at room temperature, such as those made from beef or pork gelatin. Other suitable solid dosage forms can be used, including as tablets, capsules, caplets, granules, and bulk powders. Tablets can be compressed, tablet triturates, enteric-coated, sugar-coated, film-coated, multiply compressed or multiply layered containing suitable binder, lubricants, diluents, disintegrating agents, coloring agents, flavoring agents, and preservatives. Liquid dosage forms include aqueous and nonaqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents. Specific examples of pharmaceutically acceptable carriers and excipients that may be used to formulate oral dosage forms are described in the Handbook of Pharmaceutical Excipients, American Pharmaceutical Associated (1986), the disclosure of which is incorporated herein by reference. Techniques and compositions for making tablets, capsules and pills are described in Remington's Pharmaceutical Sciences (Arthur Oxol, ed. 1980), the disclosure of which is incorporated herein by reference.

The compositions can be administered to a patient by any suitable method, and are preferably administered orally or rectally. As used herein, the term "patient" refers to any mammal, including humans, dogs and cats. A preferred dosage for adult humans is from about 1.5 grams/day to about 15 grams/day, more preferably from about 3 grams/day to about 10.5 grams/day, of the composition.

EXAMPLES

In the examples, the following tests were used:

Vickery-Voll Test:

The Vickery-Voll test is a simple test used to determine amino acid deficiencies. The three Voll Points are localized on the right foot, as shown in FIG. 1. A finger is placed on each point, one point at a time, and the right tensor fascia muscle is tested for weakening. Weakening of the muscle yields a positive result, indicating amino acid deficiencies.

Hypoglycemic Test (HOG)

The HOG test is also used to determine amino acid deficiencies. The patient is placed on his back, with his left leg extended and raised to 45 degrees. The leg muscle is tested for strength. A positive result, i.e., weakness, indicates inferred amino acid deficiencies and potential or active hypoglycemic state.

Gland Scan Test

The Gland Scan test is another amino acid deficiency test. The patient places his hands on Neuro Lymphatic points and alarm points. The patient's reflexes are read. Weakening of the muscle corroborates amino acid deficiencies and electrical polarity change in the glands tested.

BEV Test

The BEV test is used to determine the presence of spinal disk lesions. Pressure is exerted on different areas of the patient's spine (cervical, lumbar and dorsal regions), and the patient bends his spine in each region in four different quadrants. The mid-deltoid muscle is tested for strength, with weakening evidencing the presence of spinal disk lesions. The BEV test is described in more detail in Vickery, The Collected Papers of the International College of Applied Kinesiology, Summer 1990–91, Vol. I, pages 224–234, the disclosure of which is incorporated herein by reference.

Confirmatory Challenge Test (CCT)

The Confirmatory Challenge Test is also used to determine the presences of disk lesions. A description of the Confirmatory Challenge Test is provided in Vickery, Collected Papers of the Members of the International College of Applied Kinesiology-U.S.A., Summer 1989–90, Vol. I, pages 259–266, the disclosure of which is incorporated herein by reference.

Raglan Test

The Raglan Test is used to measure adrenal insufficiency. The patient's blood pressure is taken sitting, standing, and laying down. A drop in blood pressure when the patient goes from laying to sitting or from sitting to standing indicates adrenal insufficiency.

Example 1

A composition was prepared by combining the following:

| | |
|---|---|
| L-arginine base | 57 mgs |
| L-cystine | 20 mgs |
| L-histidine base | 19 mgs |
| L-isoleucine | 58 mgs |
| L-leucine | 75 mgs |
| L-lysine HCl | 53 mgs |
| L-methionine | 27 mgs |
| L-phenylalanine | 49 mgs |
| L-threonine | 42 mgs |
| L-tyrosine | 37 mgs |
| L-valine | 64 mgs |
| molybdenum* | 15 mcgs |
| creatine monohydrate | 125 mgs |
| methylsulfonylmethane | 125 mgs |

*The molybdenum was provided by Douglas Laboratories as a molybdenum composition comprising primarily dicalcium phosphate with a molybdenum complex containing sodium molybdate combined with alphaketoglutaric acid, citric acid, fumaric acid, malic acid, and succinate, to achieve a total molybdenum concentration of 1% by weight.

The components, all in powdered form, were combined in a plastic bag, which was filled with air and sealed closed. The bag was tossed and shaken for approximately 10 minutes. The mixed powder was then put into gel capsules using an encapsulation machine.

Example 2

The patient had a lumbar facet risotomy in 1990 and left knee reconstruction in 1976 and was diagnosed with Crohn's disease. An MRI revealed disk herniation between L4–L5. Additionally, the patient had burning pain down the right leg (front) and severe back pain. Surgery was scheduled two days later.

Examination revealed that the L4–L5 lesion was inactive. CCT tests revealed that T12-L1, L1–L2, L2–L3 disks were actively causing the condition. The subject was also found to have a protein deficiency, along with other nutritional deficiencies, and degenerating disks in the thoracic and cervical spine (a common finding) using the BEV tests. The subject was placed on the composition described in Example 1 six times per day, along with other nutrients, namely NESS Formula 11 (an enzyme C Complex, NESS, Riverside, Mo.), Multi Plus (multi-vitaminerals by Biotics Research Corp., Houston, Tex.), and Flax/Borage Oil (Pure Encapsulations, Sudbury, Mass.). No spinal correction was done. The patient experienced so much pain relief and healing in the two days that the operation was canceled. The patient had two chiropractic adjustments within a week. No surgery was performed, and follow-up examination one month later revealed no diskal degeneration anywhere in the spine, no sign of the Crohn's disease, and that straight posture was being maintained.

Example 3

A patient was troubled by fungus infection under both large toenails that no spray, ointment, or cream seemed to mitigate, despite a daily consumption of three grams of an enhanced amino acid formulation (containing all of the amino acids in the formulation of Example 1, but no molybdenum, sulfur or creatine monohydrate) and a full nutritional supplement spectrum of professional quality. Five months after starting on the formula described in Example 1 six to eight times per day, both toenails were pink and normal. The toenails were also softer and grew faster.

Example 4

A fifty-year-old patient was seen in 1998 for severe pains in the left shoulder, neck, and right ankle. He had previously had surgery that involved removal of bone on the left scapula with muscular reattachment. He had also had surgery on his left temporomandibular joint (TMJ) in 1982, and cervical disk surgery in 1991. Examination revealed that every BEV Test was positive throughout the spine and that the spine was in a state of severe degeneration. He also had persistent muscle injury in his left scapula, neck and right ankle. Bacterial infection was found at the neck, left scapula and the right ankle. He tested positive for Epstein Barr Virus, was vitamin C deficient (miniscurvy), and was antioxidant deficient. He also tested positive for hypoglycemia (HOG) and hyperglycemia (HYG). He was placed on a composition as described in Example 1 six times per day, Bio Multi Plus (multi-vitaminerals by Biotics Research Corp., Houston, Tex.) three times per day, Biotics Bioprotect (antioxidant formula, Biotics Research Corp.) four times per day, and NESS Formula 11 (an enzyme C Complex, NESS, Riverside, Miss.) six times per day. Within one week, the Vickery-Voll Test was negative, most of the spinal disks were healing, the infections were healing and 75% of the pains had disappeared.

Example 5

A 50-year-old female patient complained about universal allergic reaction, being subject to immediate whole body swelling, high blood pressure, being overweight, various aches and pains, headaches, and skin eruptions. She was house-bound for ten years, and her home was kept cold to avoid furnace fumes. She engaged in no physical activity and had a limited diet. She previously was athletic, having bicycled across the country, and considered becoming a professional golfer. Suddenly she became ill in 1986 and deteriorated thereafter. She saw many doctors and had all silver amalgam fillings removed.

She was examined, and BEV tests were all positive in every area of the spine, indicating severe tissue degeneration. The Vickery-Voll, HOG, Gland Scan, and Raglan tests were all positive. Epstein Barr Virus, yeast infection throughout the body, and vitamin C, fatty acid, calcium, NaCl, and B vitamin deficiencies were found. Parasites were suspected. Sensitivity to silver amalgam and formaldehyde was positive. The patient was placed on a formulation similar to that described in Example 1, but without the molybdenum, sulfur, or creatine monohydrate at an increasing rate (2/day-4/day-6/day) as tolerated, and all other deficiencies were addressed. Slow and stair-like progress took place with many exacerbations and remissions. In 1997, the patient began on a formulation as described in Example 1, beginning with one 750 mg capsule per day, gradually increasing to four capsules per day. The patient is now walking two miles a day and able to enter stores, hotels, and shopping malls. The patient now practices golf and will soon be playing again. This case demonstrates the increased detoxification ability of the formulation of Example 1 through increased sulfate metabolism in the liver as well as its tissue rebuilding aspect.

The above descriptions of exemplary embodiments of compositions and methods for enhancing protein anabolism are for illustrative purposes. Because of variations which will be apparent to those skilled in the art, the present invention is not intended to be limited to the particular embodiments described above. The scope of the invention is defined in the following claims. Further, it should be understood that the composition of the invention can function in accordance with the practice of the invention in the absence of any elements or materials not specifically described herein as being part of the composition.

I claim:

1. A composition for enhancing protein anabolism or detoxification, comprising molybdenum, at least one non-amino acid source of sulfur, and at least two amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine, wherein the composition is in oral or rectal dosage form.

2. A composition according to claim 1, wherein the molybdenum is present in the composition in an amount of from about 0.001% to about 0.03% by weight, based on the total weight of the active ingredients in the composition.

3. A composition according to claim 1, wherein the molybdenum is present in the composition in an amount of from about 0.0015% to about 0.01% by weight, based on the total weight of the active ingredients in the composition.

4. A composition according to claim 1, further comprising creatine.

5. A composition according to claim 4, wherein the creatine is present in the composition in an amount of from about 3% to about 30% by weight, based on the total weight of the active ingredients in the composition.

6. A composition according to claim 4, wherein the creatine is present in the composition in an amount of from about 12% to about 22% by weight, based on the total weight of the active ingredients in the composition.

7. A composition according to claim 1, wherein the at least one non-amino acid source of sulfur is present in the composition in an amount of from about 1.5% to about 15%, based on the total weight of the active ingredients in the composition.

8. A composition according to claim 1, wherein the at least one non-amino acid source of sulfur is present in the composition in an amount of from about 5% to about 10%, based on the total weight of the active ingredients in the composition.

9. A composition according to claim 1, comprising methylsulfonylmethane.

10. A composition according to claim 9, wherein the methylsulfonylmethane is present in the composition in an amount of from about 5% to about 45% by weight, based on the total weight of the active ingredients in the composition.

11. A composition according to claim 9, wherein the methylsulfonylmethane is present in the composition in an amount of from about 15% to about 30% by weight, based on the total weight of the active ingredients in the composition.

12. A composition according to claim 4, further comprising methylsulfonylmethane.

13. A composition according to claim 1, comprising at least three amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine.

14. A composition according to claim 1, comprising at least four amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine.

15. A composition according to claim 14, further comprising creatine.

16. A composition according to claim 1, comprising methylsulfonylmethane, L-arginine, L-cystine, L-histidine, L-isoleucine, L-leucine, L-lysine, L-methionine, L-phenylalanine, L-threonine, L-tyrosine, and L-valine, and further comprising creatine monohydrate.

17. A composition according to claim 16, further comprising L-tryptophan or 5-hydroxytryptophan.

18. A composition according to claim 16, comprising, based on the total weight of the active ingredients in the composition:
   about 6% to about 9% by weight L-arginine,
   about 2% to about 4% by weight L-cystine,
   about 1.5% to about 3.5% by weight L-histidine,
   about 6% to about 9% by weight L-isoleucine,
   about 8% to about 12% by weight L-leucine,
   about 6% to about 8% by weight L-lysine,
   about 2.5% to about 4.5% by weight L-methionine,
   about 5.5% to about 7.5% by weight L-phenylalanine,
   about 4.5% to about 6.5% by weight L-threonine,
   about 4% to about 6% by weight L-tyrosine,
   about 7% to about 10% by weight L-valine,
   about 0.001% to about 0.03% by weight molybdenum,
   about 3% to about 30% by weight creatine monohydrate, and
   about 5% to about 45% by weight methylsulfonylmethane.

19. A composition according to claim 18, further comprising L-tryptophan or 5-hydroxytryptophan in an amount of from about 0.8% to about 3% by weight, based on the total weight of the active ingredients in the composition.

20. A composition according to claim 1, comprising, based on the total weight of the active ingredients in the composition:
  about 7.3% by weight L-arginine,
  about 2.7% by weight L-cystine,
  about 2.5% by weight L-histidine,
  about 7.5% by weight L-isoleucine,
  about 9.7% by weight L-leucine,
  about 6.9% by weight L-lysine,
  about 3.5% by weight L-methionine,
  about 6.4% by weight L-phenylalanine,
  about 5.5% by weight L-threonine,
  about 4.8% by weight L-tyrosine,
  about 8.3% by weight L-valine,
  about 1.9% tryptophan or 5-hydroxytryptophan,
  about 0.002% by weight molybdenum,
  about 16.6% by weight creatine monohydrate, and
  about 16.6% by weight methylsulfonylmethane.

21. A composition according to claim 1, comprising, based on the total weight of the active ingredients in the composition:
  about 7.6% by weight L-arginine,
  about 2.7% by weight L-cystine,
  about 2.5% by weight L-histidine,
  about 7.7% by weight L-isoleucine,
  about 10% by weight L-leucine,
  about 7.1% by weight L-lysine,
  about 3.6% by weight L-methionine,
  about 6.5% by weight L-phenylalanine,
  about 5.6% by weight L-threonine,
  about 4.9% by weight L-tyrosine,
  about 8.5% by weight L-valine,
  about 0.002% by weight molybdenum,
  about 16.6% by weight creatine monohydrate, and
  about 16.6% by weight methylsulfonylmethane.

22. A composition according to claim 1, wherein the amino acids are free form amino acids.

23. A composition according to claim 18, wherein the amino acids are free form amino acids.

24. A composition according to claim 1, wherein the at least two amino acids are contained in powdered egg white or powdered milk.

25. A composition according to claim 24, further comprising a proteolytic enzyme.

26. A composition according to claim 25, further comprising creatine monohydrate.

27. A composition according to claim 1 in the form of a powder.

28. A composition according to claim 27, wherein the powder is encapsulated in a gelatin capsule.

29. A method for enhancing protein anabolism in a patient, comprising administering to the patient an effective amount of a composition according to claim 1.

30. A method according to claim 29, wherein the composition is administered to the patient in an amount of from about 1.5 grams/day to about 15 grams/day.

31. A method according to claim 29, wherein the composition is administered to the patient in an amount of from about 3 grams/day to about 10.5 grams/day.

32. A method according to claim 29, wherein the following total amounts of active ingredients are administered each day to the patient:
  L-arginine: about 0.18 to about 0.95 grams/day,
  L-cystine: about 0.06 to about 0.42 grams/day,
  L-histidine: about 0.05 to about 0.37 grams/day,
  L-isoleucine: about 0.18 to about 0.95 grams/day,
  L-leucine: about 0.24 to about 1.26 grams/day,
  L-lysine: about 0.18 to about 0.84 grams/day,
  L-methionine: about 0.07 to about 0.47 grams/day,
  L-phenylalanine: about 0.15 to about 0.79 grams/day,
  L-threonine: about 0.13 to about 0.68 grams/day,
  L-tyrosine: about 0.12 to about 0.63 grams/day,
  L-valine: about 0.21 to about 1.05 grams/day,
  molybdenum: about 0.03 to about 3.15 mg/day,
  creatine: about 0.09 to about 3.15 grams/day, and
  sulfur: about 0.15 to about 4.73 grams/day.

33. A method for enhancing detoxification in a patient, comprising administering to the patient an effective amount of a composition according to claim 1.

34. A method according to claim 33, wherein the composition is administered to the patient in an amount of from about 1.5 grams/day to about 15 grams/day.

35. A method according to claim 3, wherein the composition is administered to the patient in an amount of from about 3 grams/day to about 10.5 grams/day.

36. A method according to claim 33, wherein the following total amounts of active ingredients are administered each day to the patient:
  L-arginine: about 0.18 to about 0.95 grams/day,
  L-cystine: about 0.06 to about 0.42 grams/day,
  L-histidine: about 0.05 to about 0.37 grams/day,
  L-isoleucine: about 0.18 to about 0.95 grams/day,
  L-leucine: about 0.24 to about 1.26 grams/day,
  L-lysine: about 0.18 to about 0.84 grams/day,
  L-methionine: about 0.07 to about 0.47 grams/day,
  L-phenylalanine: about 0.15 to about 0.79 grams/day,
  L-threonine: about 0.13 to about 0.68 grams/day,
  L-tyrosine: about 0.12 to about 0.63 grams/day,
  L-valine: about 0.21 to about 1.05 grams/day,
  molybdenum: about 0.03 to about 3.15 mg/day,
  creatine: about 0.09 to about 3.15 grams/day, and
  sulfur: about 0.15 to about 4.73 grams/day.

37. A composition according to claim 1, wherein the composition is in oral dosage form.

38. A composition for enhancing protein anabolism or detoxification, comprising molybdenum, creatine and at least two amino acids selected from the group consisting of L-arginine, L-cystine, L-histidine, L-isoleucine, L-leucine, L-lysine, L-methionine, L-phenylalanine, L-threonine, L-tryptophan, L-tyrosine, and L-valine.

39. A composition according to claim 38, wherein the molybdenum is present in the composition in an amount of from about 0.001% to about 0.03% by weight, based on the total weight of the active ingredients in the composition.

40. A composition according to claim 38, wherein the creatine is present in the composition in an amount of from about 3% to about 30% by weight, based on the total weight of the active ingredients in the composition.

41. A method for enhancing protein anabolism or detoxification in a patient, comprising administering to the patient an effective amount of a composition according to claim 38.

42. A method according to claim 41, wherein the composition is administered to the patient in an amount of from about 1.5 grams/day to about 15 grams/day.

43. A method according to claim 41, wherein the composition is administered to the patient in an amount of from about 3 grams/day to about 10.5 grams/day.

* * * * *

UNITED STATES PATENT AND TRADEMARK OFFICE
CERTIFICATE OF CORRECTION

PATENT NO. : 6,203,820 B1
DATED : March 20, 2001
INVENTOR(S) : Brice E. Vickery

It is certified that error appears in the above-identified patent and that said Letters Patent is hereby corrected as shown below:

<u>Title page,</u>
Item [56], References Cited, OTHER PUBLICATIONS, "Erdmann, R. et al.," replace "Change the Way You Fell" with -- Change the Way You Feel --, "B.M. Cohen et al.," replace "alpha 1-nad beta adrenoceptors" with -- alpha 1-and beta-adrenoceptors --.

<u>Column 12,</u>
Line 20, replace "claim 3" with -- claim 33 --.

Signed and Sealed this

Second Day of July, 2002

*Attest:*

*Attesting Officer*

JAMES E. ROGAN
*Director of the United States Patent and Trademark Office*